United States Patent
Nold et al.

(10) Patent No.: US 9,880,218 B2
(45) Date of Patent: Jan. 30, 2018

(54) TEST ELECTRODE FOR ARGON PLASMA COAGULATION MEDICAL INSTRUMENT

(71) Applicant: ERBE ELEKTROMEDIZIN GMBH, Tuebingen (DE)

(72) Inventors: Bernhard Tobias Nold, Tuebingen (DE); Matthias Zenker, Tuebingen (DE); Peter Selig, Hechingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 37 days.

(21) Appl. No.: 14/518,305

(22) Filed: Oct. 20, 2014

(65) Prior Publication Data

US 2015/0108994 A1    Apr. 23, 2015

(30) Foreign Application Priority Data

Oct. 21, 2013 (EP) .................... 13189566

(51) Int. Cl.

| G01R 31/28 | (2006.01) |
|---|---|
| A61B 18/18 | (2006.01) |
| G01R 31/02 | (2006.01) |
| A61B 18/04 | (2006.01) |
| A61B 18/16 | (2006.01) |

(Continued)

(52) U.S. Cl.
CPC ........ *G01R 31/2829* (2013.01); *A61B 18/042* (2013.01); *A61B 18/18* (2013.01); *G01R 31/025* (2013.01); *A61B 18/16* (2013.01); *A61B 2017/00477* (2013.01); *A61B 2017/00725* (2013.01); *A61B 2018/00589* (2013.01); *A61B 2018/00875* (2013.01)

(58) Field of Classification Search
None
See application file for complete search history.

(56) References Cited

U.S. PATENT DOCUMENTS

| 4,200,104 A * | 4/1980 | Harris .................... A61B 18/16 |
|---|---|---|
| | | 361/42 |
| 6,569,160 B1 * | 5/2003 | Goldin ................... A61B 18/12 |
| | | 600/427 |

(Continued)

FOREIGN PATENT DOCUMENTS

| DE | 198 39 826 A1 | 3/2000 |
|---|---|---|
| EP | 1 693 014 A1 | 8/2006 |

(Continued)

*Primary Examiner* — Patrick Assouad
*Assistant Examiner* — Douglas X Rodriguez
(74) *Attorney, Agent, or Firm* — Blank Rome LLP

(57) ABSTRACT

To provide the user of an RF-surgical instrument with a non-hazardous short test operation, for example so as to test the ignitability of an argon plasma probe, provision is made for an instrument test arrangement, which is installed into a feeding medical device or into a neutral conductor connecting cable or which is provided as plug adapter, which is to be plugged between the device and the neutral conductor connecting cable. The instrument test arrangement comprises at least one or, better yet, two ignition test electrodes, which are connected to conductors of the device or of the neutral conductor cable, preferably via impedance components. The ignition test electrodes can be accessed insofar as a spark can be created simultaneously to both ignition test electrodes by means of an operational probe or an instrument.

11 Claims, 4 Drawing Sheets

(51) Int. Cl.
　　　*A61B 17/00*　　　(2006.01)
　　　*A61B 18/00*　　　(2006.01)

(56) References Cited

U.S. PATENT DOCUMENTS

| | | | | |
|---|---|---|---|---|
| 8,157,795 | B2 * | 4/2012 | Sartor | A61B 18/042 606/41 |
| 2003/0212395 | A1 * | 11/2003 | Woloszko | A61B 18/148 606/41 |

FOREIGN PATENT DOCUMENTS

| | | |
|---|---|---|
| EP | 1 764 057 A1 | 3/2007 |
| EP | 2 537 479 A1 | 12/2012 |

* cited by examiner

TEST ELECTRODE FOR ARGON PLASMA COAGULATION MEDICAL INSTRUMENT

TECHNICAL FIELD

Embodiments of the invention relate to an instrument test arrangement in particular for medical instruments for argon plasma coagulation.

BACKGROUND

Argon plasma coagulation instruments utilize a spark, which is fed from a radio frequency (RF) generator to create an argon plasma. Prior to carrying out the actual treatments, users like to carry out a short test, so as to see, whether the instrument is operational. Damaged instruments and incorrect settings can thus be identified early and the use of such instruments on the patient can be avoided. In the case of probes or instruments for argon plasma coagulation, the ignition of the spark can be impacted negatively, if the last argon gas flushing had been performed a while ago or if a reusable probe, which has already been used, is used. Users, who had been faced with inferior ignition behavior of such probes in the past, tend to check the operability, in particular the ignitability, of the probe prior to the use thereof. This course of action is often also suggested by manufacturers of probes for argon plasma coagulation, so as to ensure, in particular in the case of endoscopic probes, that they are only inserted into the endoscope or are only used on the patient, respectively, if the probe or the instrument, respectively, works correctly as well as if matching settings were selected on the device.

A probe cannot simply be tried out on the patient, because injuries can be caused by this. The ignition test on metal parts, which are grounded in an undefined manner, is improper, because it can lead to injuries to patient and personnel as well as to damages to electrical and electronic equipment. It can nonetheless not be excluded that users carry out such improper tests.

From practice, ignition test adapters are known, which were brought on the market by the owner of the instant property right. Instead of the neutral electrode, such an ignition test adapter is to be plugged into the neutral socket of the feeding device and it comprises an electrode, which is grounded in a defined manner. A replugging at the device is thus required. This can have the result that the ignition test adapter is not used and that the user either does not carry out an ignition test or uses points, which are grounded in an undefined manner (equipment trolleys, infusion stands) for the ignition test after all again.

Based on this, it is the object of embodiments of the invention to specify a concept, by means of which the operability, in particular the ignitability, of an instrument or of a probe can be tested prior to the use on the patient in a comfortable manner.

For this purpose, embodiments of the invention provide for an instrument test arrangement, by means of which the probe or the medical instrument can be tested without any danger under defined conditions. The instrument test arrangement can be embodied as modified neutral conductor cable, as plug adapter or can be embodied at the feeding device itself.

The neutral conductor cable includes a connector for the neutral connection of the medical device. The flexible neutral conductor cable extends from the connector to a neutral electrode connection or to a neutral electrode arrangement. In one embodiment, the instrument test arrangement is arranged at the neutral conductor cable. The instrument test arrangement includes an ignition test electrode support, which comprises at least one ignition test electrode, which is connected electrically to the conductor of the cable.

The ignition test electrode support can be attached to the connector, can be built into the connector, can be embodied as part of the connector, can be arranged in the path of the flexible cable section or also at the neutral electrode connection or at the neutral electrode arrangement. The ignition test electrode support includes at least one ignition test electrode, which is connected electrically to the at least one conductor of the flexible cable section.

If the instrument test arrangement is embodied as plug adapter, it has a plug on the side of the device, where it is to be plugged in, and a socket on the side of the cable. Provision can be made between both for a rigid housing or for a cable section. In the latter case, the plug adapter forms a neutral conductor extension cable. The ignition test electrodes can be arranged at any suitable location of the plug adapter.

If the instrument test arrangement is embodied at the device itself, it can comprise one or two ignition test electrodes. If it has only one ignition test electrode, the latter is connected to the neural conductor, which leads to a split stage, which divides the neutral conductor into at least two conductors, which lead to partial electrodes of the neutral electrode arrangement. The split stage has the object of monitoring the correct attaching of the partial electrodes to a patient by means of resistance or impedance test. If the instrument test arrangement has two ignition test electrodes, they can be connected downstream from the two neural conductors, which lead to the two-pole or multi-pole neutral socket and from there to the neutral electrode arrangement via the neutral conductor cable.

In the case of all of the above-mentioned concepts, it is ensured that the circuit of the electric spark, which is ignited as an experiment, does not include the patient, so that negative impacting of the patient is impossible. The test can furthermore be carried out without having to remove the neutral electrode from the patient or the connector from the device. The instrument test arrangement according to embodiments of the invention thus also allows for the operational test in a busy environment with minimum expenditure of time.

The neutral conductor cable preferably comprises two (or more) neutral conductors, which extend from the device or from the plug to the neutral electrode connection or to the neutral electrode arrangement. Preferably, a neutral electrode, which is divided into a plurality of (at least two) partial electrodes, is used. The correct attaching of the two partial electrodes to the patient can be tested by measuring the impedance or the resistance between the two partial electrodes. Preferably, the feeding device includes a corresponding test connection, which measures the resistance between the two conductors and thus between the two partial electrodes attached to the patient. In the case of such a concept, the ignition test electrode support in each case comprises at least one ignition test electrode, which is connected electrically to the conductor, for each conductor. The connection between the ignition test electrode and the conductor is preferably established via a component comprising an electrical impedance, preferably comprising a resistive or capacitive characteristic. In so doing, it is avoided that the spark, which is ignited as an experiment, short-circuits the two conductors with one another or only contacts one of the conductors. Both cases could otherwise lead to an activation of a monitoring system, which tests the correct attaching of the partial electrodes of the neutral electrode arrangement.

Further details of advantageous embodiments of the invention are the subject matter of claims, the description and/or the drawings.

DETAILED DESCRIPTION

Figure 1:
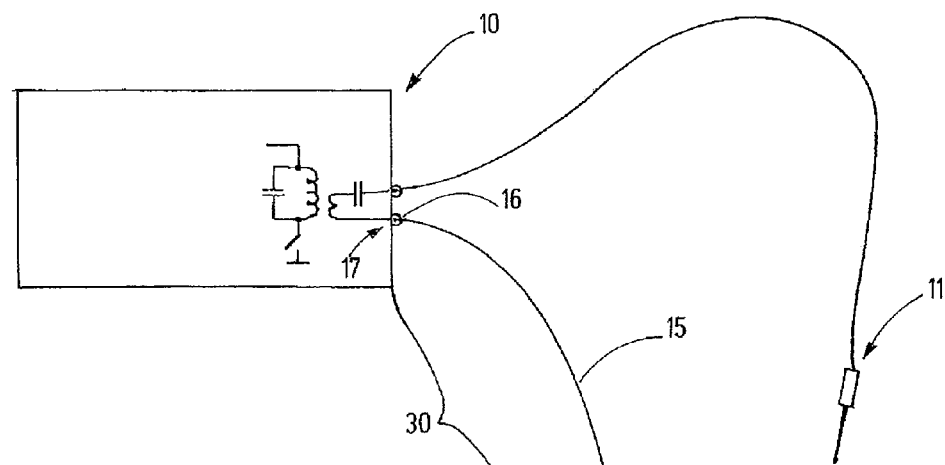
FIG. 1 shows a medical device for feeding an RF-surgical instrument as well as a neutral conductor cable for connecting a neutral conductor arrangement to the device in schematic illustration.

FIG. 1 illustrates a medical device 10 for feeding an electrosurgical instrument 11, which acts on biological tissue. The instrument 11 can be an instrument, which is used in open surgery, for laparoscopy or also for endoscopy, a so-called probe. In particular, the instrument 11 can be an argon plasma coagulation probe.

The current, which is introduced into the biological tissue by means of the instrument 11, is returned to the device 10 via a neutral electrode arrangement 12. The neutral electrode arrangement 12 comprises at least one, preferably two or more partial electrodes 13, 14, which belong to a neutral conductor cable 15 or which are connected to the latter. The neutral conductor cable 15 establishes a flexible connection between the neutral electrode arrangement 12 and the device 10. At its end on the side of the device, the neutral conductor cable 15 comprises a connector 16, which is plugged into the neutral socket 17 of the device 10.

Figure 2:
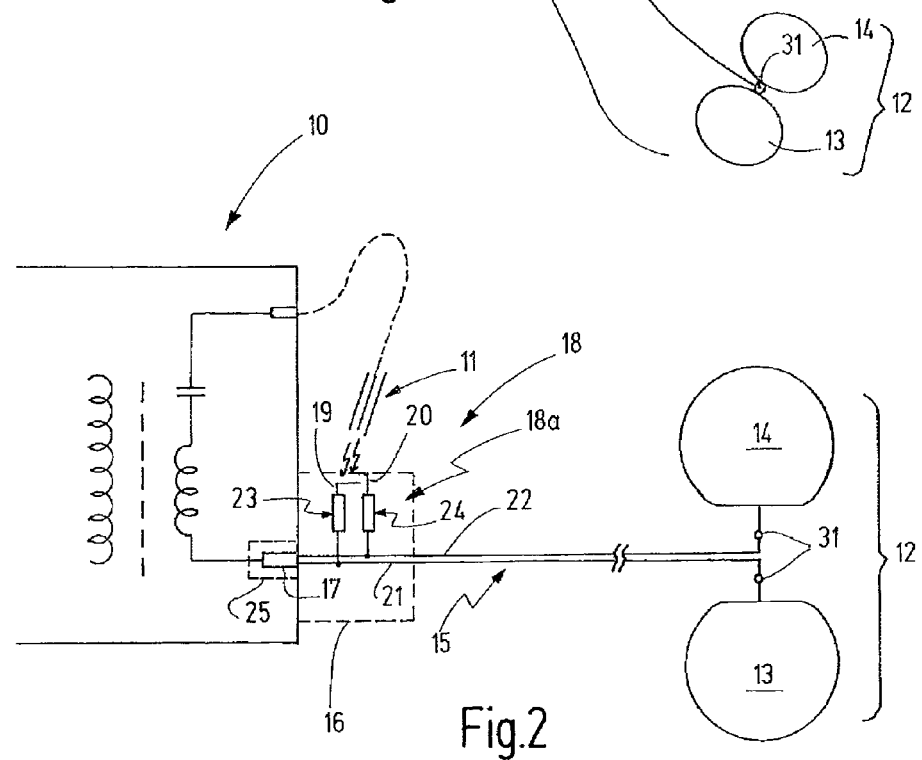
FIG. 2 shows the device and the neural cable comprising instrument test arrangement in schematized illustration.

As is shown in FIG. 2, the neutral conductor cable 15 can be provided with an instrument test arrangement 18, which serves the purpose of being able to test the ignitability and operability of the instrument 11.

The instrument test arrangement 18 comprises at least one, preferably two ignition test electrodes 19, 20, which are connected electrically to conductors 21, 22 of the neutral conductor cable 15. The ignition test electrode 19 is connected to the conductor 21, preferably via an impedance component, for example a resistive, preferably an ohmic component 23. The resistance can be 20 Ohm, for example. Preferably, it lies within the range of between 10 and 50 Ohm. The ignition test electrode 20 is preferably also connected to the conductor 22 via a corresponding impedance component 24. Its resistance, in turn, preferably lies within the range of between 10 Ohm and 50 Ohm, for example 20 Ohm. The two impedance components 23, 24 can be embodied equally or also slightly differently.

The conductor 21 is connected to the first partial electrode 13. The conductor 22 is connected to the second partial electrode 14. A split circuit 25 is suggested only schematically in FIG. 2 and serves the purpose of measuring the ohmic resistance or the impedance between the two partial electrodes 13, 14. In this manner, it is determined, whether both partial electrodes 13, 14, and thus the entire neutral electrode arrangement 12, comprises a sufficient electrical contact to the patient.

Figure 9:
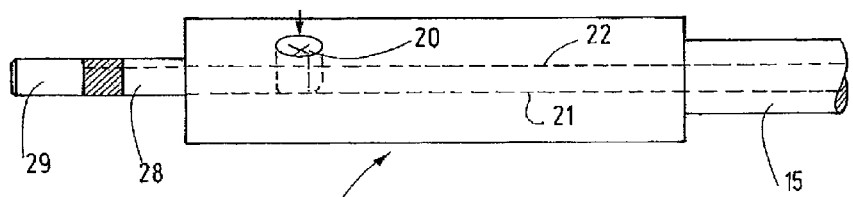
FIG. 9 shows a connector as part of an instrument test arrangement in schematic side view and FIGS. 10 to 14 show different embodiments of instrument test arrangements in each case in schematic illustration.
Figure 11:
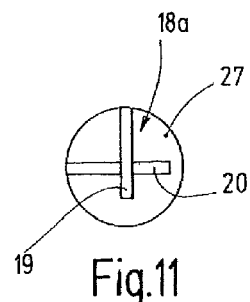

The instrument test arrangement 18 comprising the two ignition test electrodes 19, 20 can be arranged in the connector 16, which is suggested in FIG. 2 only in a schematic manner by means of dashes. It is illustrated somewhat more solidly in FIG. 9, wherein the reference numerals, which have already been introduced, are assumed and used. The connector 16 can consist of a plastic material or another insulating material, which forms an insulator body 26. The connector 16 can also comprise a metal housing, into which a corresponding insulator body is inserted. A depression 27, in which the two ignition test electrodes 19, 20 are arranged, can be embodied in the insulator body 26. As is shown in FIG. 11, for example, the ignition test electrodes 19, 20 can be formed by means of two metal needles or wires, which cross one another at a slight distance. The illustration of the impedance components 23, 24 was forgone in FIG. 9. It can be seen, however, that the two conductors 21, 22 are guided to different contacts 28, 29 of a connector pin, which projects away from the connector 16. When being used, the connector pin is plugged into the neutral electrode socket of the device.

The device 10 and the instrument 11 as well as in particular the instrument test arrangement 18 operate as follows:

To carry out a treatment with the instrument 11, the latter is initially connected to the device 10, as is illustrated in FIG. 1. In addition, the neutral electrode arrangement 12 is attached to the human or animal patient. The user will then want to test the operability and in particular the ignitability of the instrument 11. For this purpose, he brings the distal end of the probe or of the instrument 11 in the vicinity of the depression 27 and then activates the generator of the device 10. If the instrument 11 is ignitable, a spark jumps to the ignition test electrodes 19, 20, wherein the current, which thus flows as an experiment, discharges via both conductors 21, 22 to the device 10. The neutral electrode arrangement 12 remains on ground potential. Due to the even current sharing, the split circuit 25 does not detect an error signal. It sees the same relationships as in the case of surgery or treatment at the patient.

In the case of the instant exemplary embodiment, the instrument test arrangement 18 is part of the connector 16 and thus part of a neutral conductor connecting cable 30. The latter includes the connector 16, the neutral conductor cable 15 as well as the neutral electrode arrangement 12. In the alternative, it is also possible that, instead of the neutral electrode arrangement 12, only a neutral electrode connection 31 belongs to the neutral conductor connecting cable 30, to which one or a plurality of neutral electrodes are to be connected.

Figure 3:
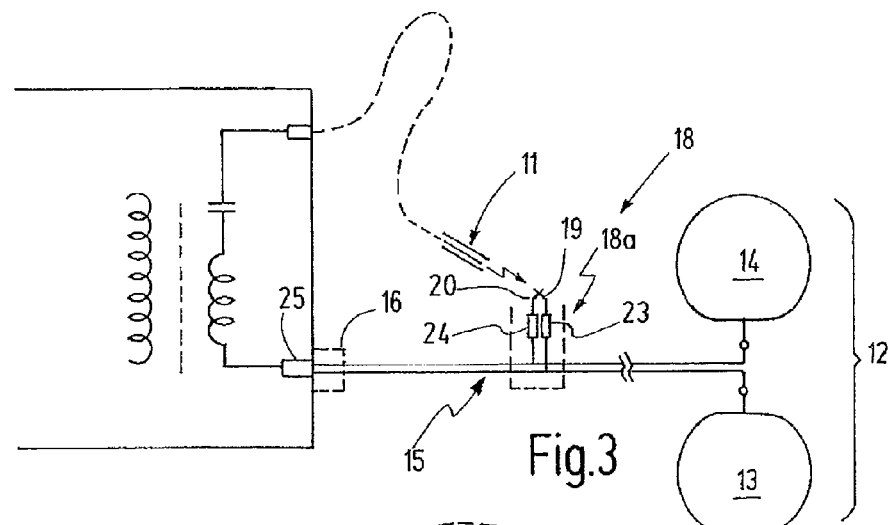
FIGS. 3 to 8 show modified instrument test arrangements according to embodiments of the invention in schematic illustration.

The instrument test arrangement 18 does not necessarily need to be arranged at the connector 16. It can nonetheless be part of the neutral conductor connecting cable 30. An exemplary embodiment for this follows from FIG. 3. As can be seen, the instrument test arrangement 18 can be arranged in the path of the neutral conductor cable 15 between the connector 16 and the neutral electrode arrangement 12. For this purpose, the instrument test arrangement 18 can comprise its own insulating housing, which is not illustrated further, in or at which the ignition test electrodes 19, 20 are arranged. A modified instrument test arrangement according to FIG. 3 can also comprise a connection possibility for the neutral electrode cable 15, so that the neutral electrode cable 15 is embodied in two parts. A first part of the neutral electrode cable 15, which is a part of the instrument test arrangement 18, leads from the latter to the device 10. A second part of the neutral electrode cable 15 is releasably connected to the instrument test arrangement 18, for example by means of a plug-in connection and leads from the latter to the neutral electrode.

Figure 4:
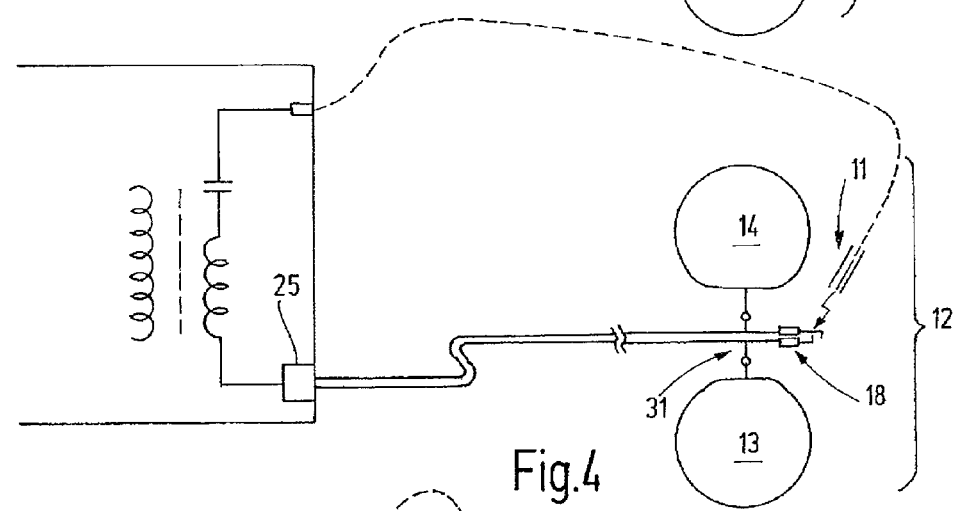

As shown in FIG. 4, the instrument test arrangement 18 can also be arranged at the neutral electrode arrangement 12, for example at the neutral electrode connection 31. The instrument test arrangement 18, in turn, can comprise its own insulator housing or can be arranged in the neutral electrode connection 31, for example.

Figure 5:
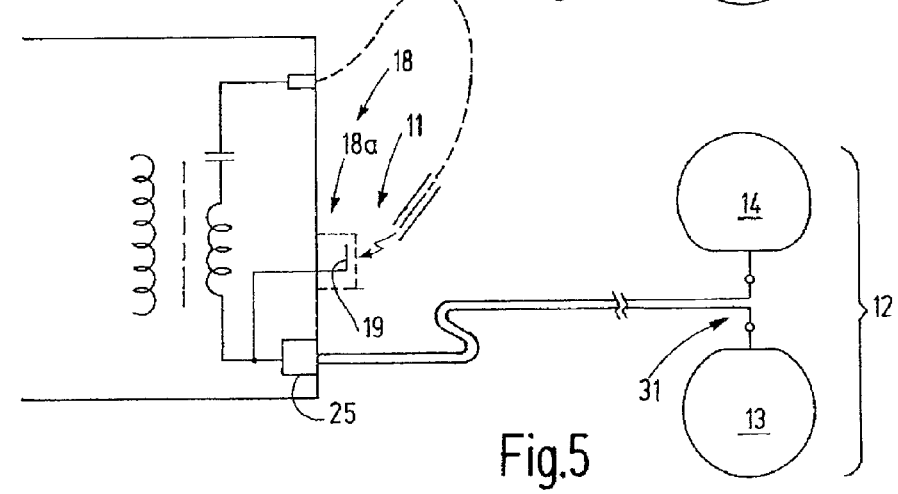

In the case of a modified embodiment according to FIG. 5, the instrument test arrangement 18 is embodied as part of the device 10. The ignition test electrode 19 is connected to the neutral conductor upstream of the split circuit 25. In this case, a single ignition test electrode, which is arranged in an insulator housing in a recess, is sufficient.

Figure 6:
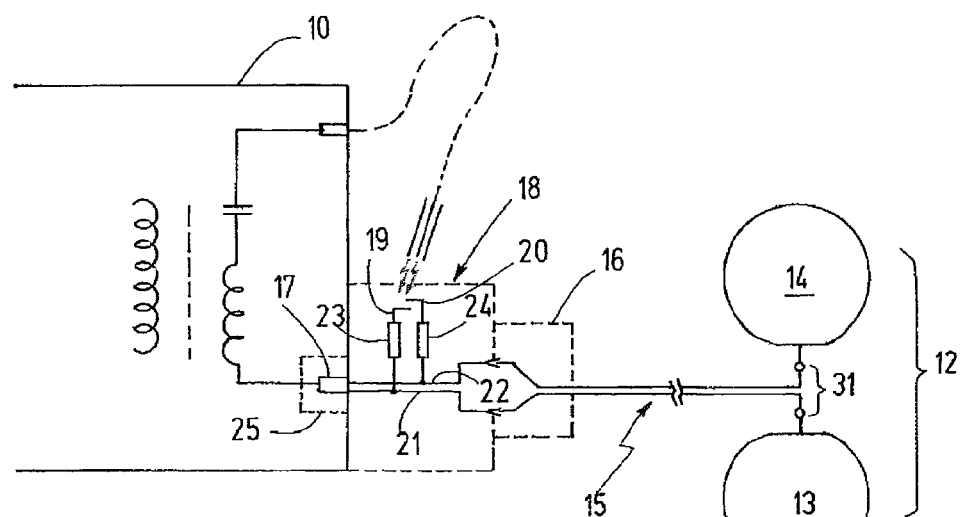

In the case of a further modified embodiment according to FIG. 6, the instrument test arrangement 18 is embodied as plug adapter, which is arranged between the connector 16 and the neutral socket 17. It can comprise its own insulating material housing, in which the ignition test electrodes 19, 20 and the impedance components 23, 24, are arranged, in turn. The conductors 21, 22 lead to a socket arrangement, which is provided at the plug adapter and into which the connector 16 is to be inserted. Otherwise, the above description applies accordingly.

Figure 7:
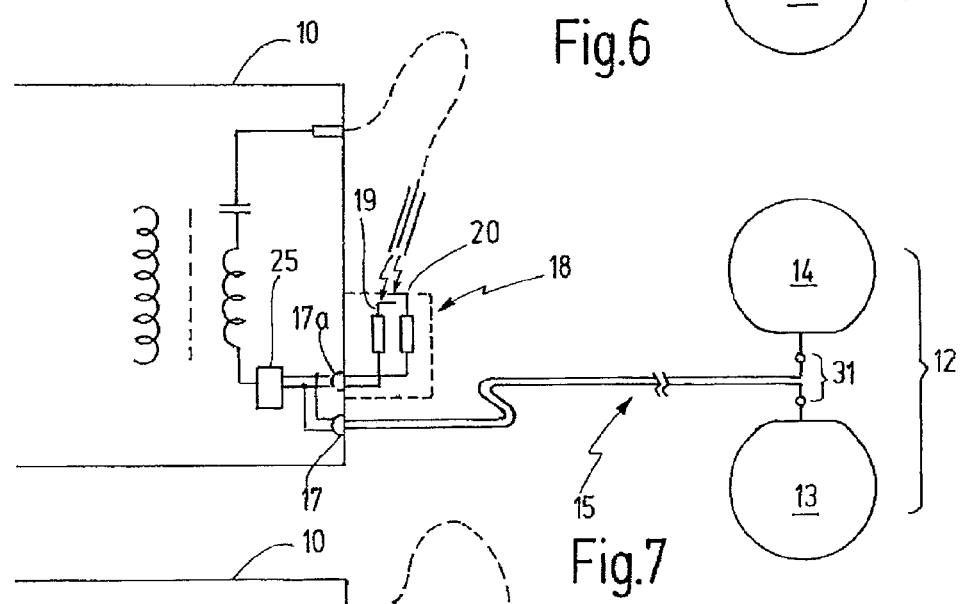

The instrument test arrangement 18 can also be arranged at a separate socket 17a, which, according to FIG. 7, is provided at the device 10 and which is switched electrically parallel to the socket 17. The instrument test arrangement 18, which, with the two test electrodes 19, 20, provides the user with a possibility for trying out a probe or his instrument, can be plugged into this separate socket 17a, in turn. The above description also applies accordingly with regard to this in a supplementary manner.

Figure 8:
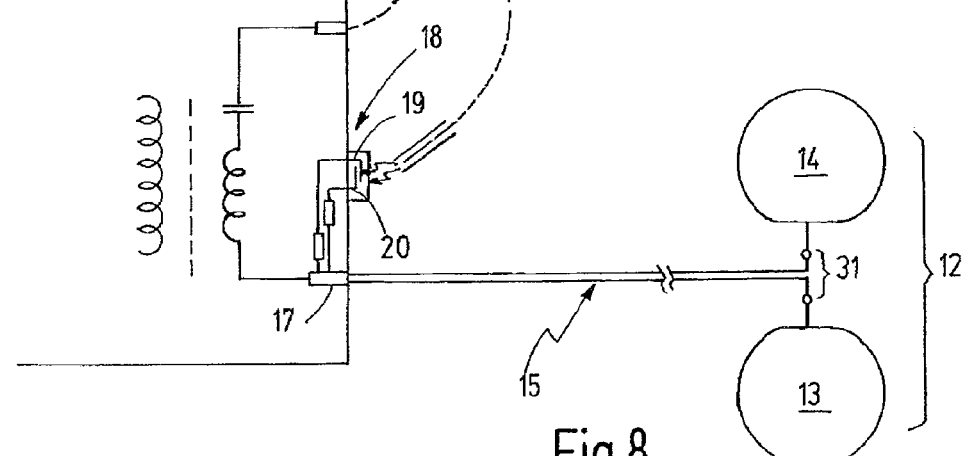

A further embodiment follows from FIG. 8. The instrument test arrangement 18 is installed into the device 10 similarly as in FIG. 5. However, provision is made for two ignition test electrodes 19, 20, which are arranged in or at the device 10. For this purpose, the device 10 can comprise a corresponding insulator material body, which accommodates the two ignition test electrodes 19, 20, which, in turn, are exposed in a depression, for example. The above description applies in a supplementary manner.

Figure 10:
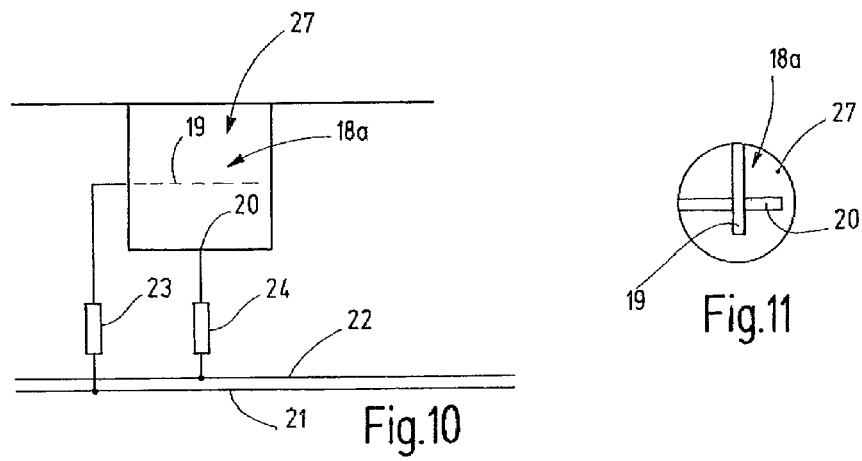

To supplement the description, reference is made to FIGS. 11 to 14. Contrary to the illustration in FIG. 11, the ignition test electrodes 19, 20 can comprise a variety of different shapes. According to FIG. 10, ignition test electrodes 19, 20, which are arranged in the depression 28, can have different designs, for example. The ignition test electrode 19 can be embodied as wire or tip or as screen or mesh, respectively, below which the ignition test electrode 20 is arranged as screen, mesh, wire, conductive surface or conductive bowl.

Figure 12:
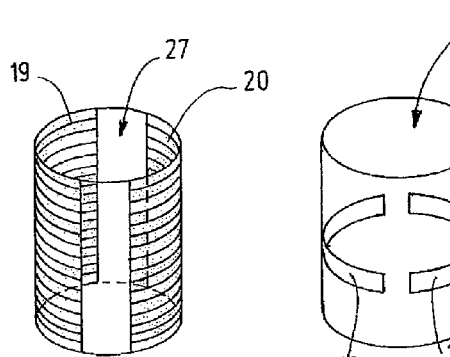

In the alternative, it is possible to attach the ignition test electrode 19, 20 to the wall of a depression 27. For this purpose, FIG. 12 illustrates an embodiment for this purpose, in the case of which the ignition test electrodes 19, 20 are arranged in a bowl-shaped manner at the circumference of the cylindrical depression 27.

Figure 13:
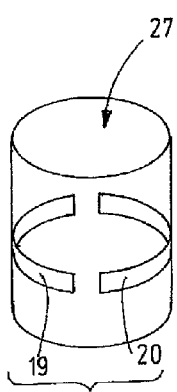

In the alternative, the ignition test electrodes 19, 20, as shown in FIG. 13, can be arranged at the inner wall of the depression 27 as narrow curved strips, which, in turn, are spaced apart from one another in circumferential direction.

Figure 14:
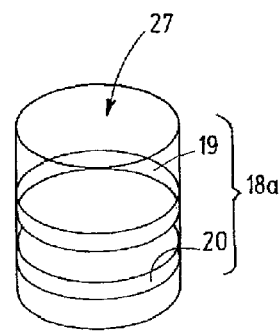

It is also possible to embody the ignition test electrodes 19, 20 as axially distanced rings, as is shown in FIG. 14.

Further combinations of available presented electrode shapes are also possible, for example the arrangement of a ring-shaped ignition test electrode in combination with a needle or rod-shaped ignition test electrode according to FIG. 11.

To provide the user of an RF-surgical instrument 11 with a non-hazardous short test operation, for example so as to test the ignitability of an argon plasma probe, provision is made for an instrument test arrangement 18, which is installed into a feeding medical device 10 or into a neutral conductor connecting cable 30 or which is provided as plug adapter, which is to be plugged between the device 10 and the neutral conductor connecting cable 30. The instrument test arrangement 18 comprises one or a plurality of ignition test electrodes 19, 20, which are connected to conductors 21, 22 of the device 10 or of the neutral conductor cable 30, preferably via impedance components 23, 24. The ignition test electrodes 19, 20 can be accessed insofar as a spark can be created simultaneously to both ignition test electrodes 19, 20 by means of an operational probe or an instrument 11.

What is claimed as new and desired to be protected by Letters Patent of the United States is:

1. An instrument test arrangement, in particular for medical instruments for argon plasma coagulation, comprising:
    an electrode arrangement configured to test a medical instrument, the electrode arrangement comprising a first ignition test electrode and a second ignition test electrode that are arranged adjacent to one another and are connected electrically to respective first and second neutral conductors of a flexible neutral conductor cable or of a device,
    wherein the first and second neutral conductors are insulated against one another and are connected to respective first and second partial electrodes of a neutral electrode arrangement and to a split circuit configured to measure the ohmic resistance or impedance between the first and second partial electrodes, and
    wherein the first and second partial electrodes are configured for attachment to a patient.

2. The instrument test arrangement of claim 1, wherein the electrode arrangement is part of a connector, which comprises at least one contact for connecting to a medical device, so that the first and second ignition test electrodes are arranged in or at the connector, wherein the flexible neutral conductor cable extends away from the connector to the neutral electrode arrangement or a neutral electrode connection.

3. The instrument test arrangement of claim 2, wherein the connector comprises a body, which is embodied of an insulator material and which supports the first and second ignition test electrodes.

4. The instrument test arrangement of claim 3, wherein the connector comprises a plug body, which is embodied of an insulator material.

5. The instrument test arrangement of claim 1, wherein the electrode arrangement is arranged at the flexible neutral conductor cable between a connector and the neutral electrode arrangement or a neutral electrode connection.

6. The instrument test arrangement of claim 1, wherein the electrode arrangement is arranged at a neutral electrode connection or the neutral electrode arrangement, which are connected to a connector via the flexible neutral conductor cable.

7. The instrument test arrangement of claim 1, wherein the instrument test arrangement is arranged in or at the device, which serves to feed the instrument or that the instrument test arrangement is embodied as plug adapter, which is to be arranged between a neutral socket of the device and a connector of the neutral conductor cable.

8. The instrument test arrangement of claim 1, wherein the first and second ignition test electrodes are connected to the respective first and second neutral conductors via respective first and second components, which each comprises an impedance.

9. The instrument test arrangement of claim 8, wherein the first and second components each comprises a capacitance.

10. The instrument test arrangement of claim 8, wherein the first and second components each comprises an ohmic resistance.

11. The instrument test arrangement of claim 8, wherein the first and second components comprise the same electrical characteristics.

* * * * *